United States Patent [19]

Habdas et al.

[11] 4,422,233
[45] Dec. 27, 1983

[54] METHOD FOR PRODUCING HIGH TEMPERATURE ELECTRICAL CONNECTION

[75] Inventors: Edward P. Habdas; Jon D. Aaron, both of Decatur; Timothy H. Whitten, Hartselle, all of Ala.

[73] Assignee: UOP Inc., Des Plaines, Ill.

[21] Appl. No.: 429,339

[22] Filed: Sep. 30, 1982

Related U.S. Application Data

[62] Division of Ser. No. 297,908, Aug. 31, 1981, Pat. No. 4,378,279.

[51] Int. Cl.³ ............................................. H01G 9/24
[52] U.S. Cl. .................................. 29/570; 29/592 R; 264/61
[58] Field of Search ................. 29/570, 592 R, 829, 29/845, 850, 851, 863, 872, 873; 174/74 R, 75 R; 204/426; 264/61

[56] References Cited

U.S. PATENT DOCUMENTS 4,229,275  10/1980  Habdas et al. ............... 204/426

Primary Examiner—G. Ozaki
Assistant Examiner—Alan E. Schiavelli
Attorney, Agent, or Firm—James R. Hoatson, Jr.; Barry L. Clark; William H. Page, II

[57] ABSTRACT

Improved lead attachment method accommodates a situation wherein electrical signal leads must be connected to portions of a circuit operating at high temperatures such as 900° F. or more and terminate in equipment operating at or near ambient temperatures. For example, in solid electrolyte oxygen sensors incorporating a tubular ceramic member, a connection wire which is sufficiently thick to resist wire breakage during normal handling has been found to be too thick to bond to a connection pad on the ceramic without having the bond crack during thermal cycling. With improved method, a thin wire is attached to a thicker one in a region where flexing cannot occur. At least the larger wire is shrunk-fit into a hole formed in the ceramic before firing, and then the thinner wire is bonded to the pad with a conductive paste which must also be fired.

10 Claims, 7 Drawing Figures

METHOD FOR PRODUCING HIGH TEMPERATURE ELECTRICAL CONNECTION

This is a division of application Ser. No. 297,908, filed Aug. 31, 1981, now U.S. Pat. No. 4,378,279.

BACKGROUND OF THE INVENTION

The invention relates to the attachment of electrical signal leads to portions of an electrical circuit. In particular, the invention is concerned with the attachment of leads to a circuit that operates at relatively high temperatures of about 900° F. or higher, but is connected to equipment that operates at or near ambient temperature. A particular application is that of a solid electrolyte type of oxygen sensor. In one such type of device, a voltage which is generated between porous platinum electrodes affixed to opposite faces of a yttrium stabilized zirconia disc must be connected to an instrument amplifier. The disc and its electrodes typically operate at temperatures in excess of 900° F. An example of such a sensor can be found in Habdas and Aaron U.S. Pat. No. 4,229,275. In said sensors, a previously fired stabilized zirconia disc is placed into an unfired ceramic tube and sealed thereto by shrinkage of the tube as it is fired at about 2400° F. Platinum paste stripes are then painted along the inside surface of the tube and a glass frit contained within the paste securely bonds to the ceramic tube and the electrodes as the assembly is additionally fired at a temperature of about 1800° F. Preferably, the ends of the stripes terminate in enlarged pads. If the ends of the sensor containing the pads can be maintained at temperatures below about 400° F., connections to the pads can be made by ordinary solder connections or mechanical connectors. However, in many cases, low temperatures cannot be maintained and the temperature approaches the high operational temperature of the zirconia disc. In such a situation, mechanical connectors are difficult to use, and high temperature silver solders cannot be readily applied.

One attempted solution was to take a platinum lead wire of about 0.010" diameter and fire it into the platinum paste pad. The resulting bond was extremely good, but the lead wire was extremely weak from a mechanical standpoint and would break after several flexings at its point of connection. When the diameter was increased to about 0.020" to provide more mechanical strength, it was found to resist flexural breaking but would break away from the pad and ceramic when subjected to thermal shock stresses since the glass frit paste seems to more firmly adhere to the high expansion rate ceramic rather than to the platinum wire which expands less. Even when small and large diameter holes were drilled in the ceramic before firing and small and large diameter wires were shrunk-fit into them and bonded to the pads with platinum paste, the thinner wires broke when flexed and the paste broke away from the thicker wires when thermally cycled several times between room temperature and 900° F.

SUMMARY OF THE INVENTION

It is among the objects of the present invention to provide a high temperature electrical lead connection which will have sufficient strength to resist breakage due to flexing during handling while maintaining a bond to a painted lead stripe on a member which has a substantially different coefficient of temperature expansion and is subjected to high temperatures. These and other objects are provided by the connection and method of making same, of the present invention. The improved connection as it can be used in an oxygen sensor, is made by first selecting a larger diameter lead wire of platinum or another metal that can withstand the firing temperatures such as about 2400° F., of a particular ceramic which undergoes shrinkage during firing. The wire diameter should be large enough to withstand considerable flexing during use even though it is too large to be retained in contact with a conductive stripe on the ceramic by means of a platinum and glass frit paste when subjected to thermal shock. A size of about 0.020" has been found to be quite suitable. A smaller diameter lead wire of platinum or other suitable metal is also selected which is thin enough that it can withstand the thermal shock stresses without breaking its bond but is too thin to resist flexing. A size of about 0.005" has been found to be quite suitable. A hole is then drilled in the unfired or green ceramic member adjacent the places where it is desired to establish an electrical connection. The hole should be slightly larger than the combined diameters of the large and small wires to facilitate the assembly of the wires in the hole. However, the hole should not be so large that it cannot produce a 1–10% shrink fit retention of the wires as the ceramic shrinks during firing. The inside of the tube then has longitudinal platinum, glass frit paste stripes applied on opposing sides between the electrode surfaces of the solid electrolyte disc and a point immediately adjacent the holes containing the lead wires. The thin wires are then bent over and buried in the platinum paste and the entire unit is fired to about 1800° F. to fuse the conductive glass frit stripes to the ceramic body and to the thin wires.

Where the holes pass radially through the walls of the tube, the small wires can be attached to the large wires in at least two alternate fashions. In one, the large wire can be shrunk-fit in the hole and the small wire can be welded at one end to the inner end of the large wire and buried in the platinum paste stripe at its other end. In another, one end of the small wire can be wrapped around an inwardly projecting portion of the large wire and coated with platinum paste while its other end is buried in the platinum paste stripe. In all cases, it is important that the smaller diameter wire be attached to the larger one in a region which would not be subject to flexing during use.

DETAILED DESCRIPTION OF THE DRAWINGS

Figure 1:
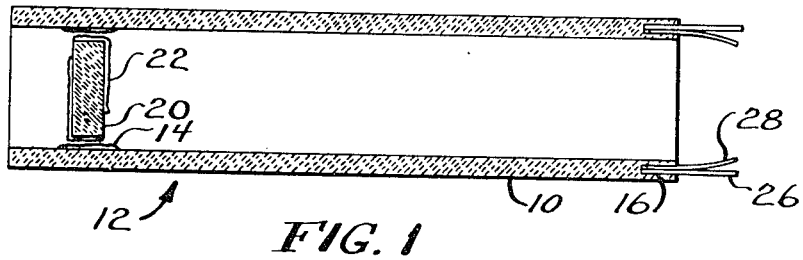
FIG. 1 shows an axial cross-section of an assembly of a tubular ceramic oxygen sensor housing, electrolyte disc, and lead connection wires as they appear prior to firing.

FIG. 1 illustrates the first step of providing an improved lead connection to the tubular ceramic body 10 of an oxygen sensor 12. The body 10 is formed of a ceramic such as forsterite, which in the green or unfired state shown, has a pair of short stripes 14 of electrode paste material applied on its interior surface and a pair of elongated openings 16 drilled in its reference end. A previously fired disc 20 of solid electrolyte material such as stabilized zirconia has conductive paste electrodes 22 applied to its opposed surfaces which become integrally bonded to the short stripes 14 as the ceramic body shrinks by up to about 25% as it is fired to about 2400° F. The holes 16 are preferably drilled slightly oversize to facilitate side by side insertion of the primary or large diameter lead wire 26 and the secondary or small diameter lead wire 28. Diameters of the wires 26, 28 of about 0.020" and 0.005", respectively, have been found to be quite satisfactory, with the holes 16 being sized so as to produce about a 1–10% shrink-fit engagement with the wires after firing.

Figure 2:
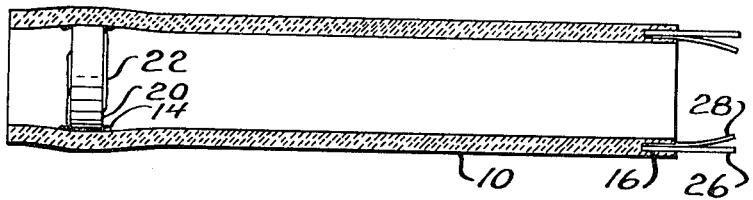
FIG. 2 shows the assembly of FIG. 1 after the lead wires and disc have been shrunk-fit into contact with the ceramic housing by firing.
Figure 3:
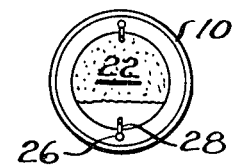
FIG. 3 is a view of the right end of the assembly shown in FIG. 2.
Figure 4:
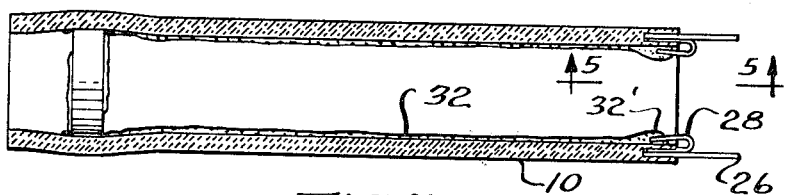
FIG. 4 shows the assembly of FIG. 2 after the inner lead stripes have been painted onto the tube and the small diameter wires have been embedded in them.
Figure 5:
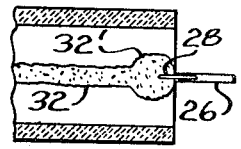
FIG. 5 is a section taken on line 5—5 of FIG. 4.

FIG. 2 shows the structure of FIG. 1 after it has been fired to about 2400° F., causing the ceramic tube 10 to shrink into engagement with the electrolyte disc 20, and causing the walls of the hole 16 to shrink into tight engagement with the wires 26, 28. The firing operation also changes the surface of the ceramic tube 10 from the somewhat glazed nature it assumes in the unfired state to a porous nature. Because the fired porous surface is much easier to coat and satisfactorily bond to the conductive paste stripes 32, the latter are preferably not applied until after firing the ceramic, as shown in FIG. 4. The paste stripes 32 preferably have an enlarged terminal pad portion 32' in which the small diameter lead 28 is embedded before the unit is again fired. This final firing is done at a temperature of about 1800° F., and serves to fuse the glass frit in the paste stripes 32, thus bonding the stripes to the ceramic tube 10 and to the lead wires 28.

Figure 6:
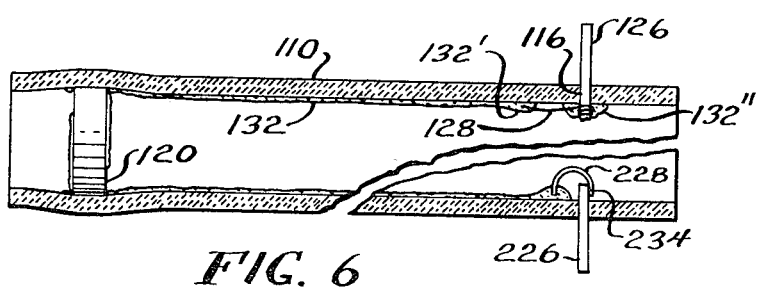
FIG. 6 is similar to FIG. 4, but shows two alternate ways to attach a lead connection wire to a painted conductive stripe.
Figure 7:
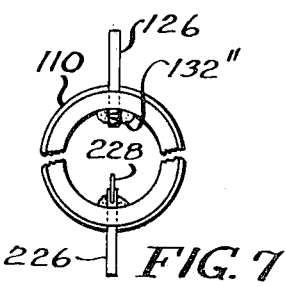
FIG. 7 is a view of the right end of the assembly shown in FIG. 6.

FIG. 6 shows two alternate modifications by which a primary lead member 126 or 226 can be attached radially to a shrinkable ceramic member 110. The large diameter leads 126 or 226 are placed into slightly oversize holes 116 formed in the member 110 before it is fired. During firing, the inside walls of the holes shrink into tight contact with the leads. Small diameter secondary wires 128 or 228 are then embedded in the terminal portions 132' of the conductive glass frit paste stripes 132 and fused as discussed in connection with FIG. 4. The secondary lead wire 128 is shown as being attached to the lead 126 by being wrapped around it and fused with a small quantity of paste 132". The secondary lead wire 228 is shown as being attached by a weld 234.

As can be noted from the preceding description, the improved electrical connections and methods of producing them disclosed herein provide electrical lead connections which include a wire lead member which is thick enough to be very resistant to breakage from flexing during use. However, since such a lead member cannot be readily attached by a conductive paste to a conductive lead stripe on a ceramic member having a different coefficient of temperature expansion without breaking its bond due to thermal shock after only a few heating cycles, the invention teaches several ways to overcome the problem by using a thin wire to contact the conductive stripe and then attaching the thin wire to the thick one in a region where flexing would not be encountered during use.

We claim as our invention:

1. An improved method for attaching a lead wire of considerable thickness to a surface of a ceramic member which shrinks when fired and which then undergoes considerable thermal expansion relative to the wire during use comprising the steps of: selecting a length of a primary lead connection wire having a sufficient thickness to withstand substantial flexure after assembly to the ceramic member but too much thickness to be capable of maintaining a glass frit bond with said surface of said member during repeated cyclings of the member to elevated temperatures; selecting a length of a secondary lead attachment wire having a thickness which is insufficient to withstand substantial flexure after assembly to the ceramic member and small enough to be capable of maintaining a glass frit bond with said member after said member expands at a different rate than said secondary lead wire when heated repeatedly during use; attaching one end of said secondary lead attachment wire relative to said primary lead attachment wire so it contacts said primary wire at a location where said primary wire cannot be flexed after assembly; forming an opening in said ceramic member and placing at least said primary wire in said opening before said ceramic member is fired; firing said ceramic member to cure it and to cause the inside surface of said opening to shrink and lockingly engage at least said primary wire; applying a coating of conductive frit to said surface of the ceramic member and to the other end of said secondary wire after it is bent over into contact with said surface; and again firing said ceramic member frit and lead wire assembly to fuse said conductive frit and bond said secondary lead wire to said surface.

2. The method of claim 1 wherein said ceramic member is a tube which has a pair of glass frit conductive stripes applied to it along at least a portion of its internal length at spaced circumferential locations prior to the last firing step each of said stripes being connected to a sensing device at one of its ends and to a bentover end of a secondary wire at its other end.

3. The method of claim 1 wherein said one end of said secondary lead attachment wire is in parallel contacting relationship with said primary wire within said opening and is also lockingly engaged by the inside surface of said opening.

4. The method of claim 1 wherein said one end of said secondary lead attachment wire is attached by welding to said primary wire.

5. The method of claim 1 wherein the said one end of said secondary lead attachment wire is attached to said primary wire by being wrapped around it and by being coated with a layer of conductive glass frit which fuses the wires together during the last firing step.

6. An improved method of assembling a lead connection to the reference end of an oxygen sensor of the type having a generally tubular ceramic body which is closed at a sensing end by a portion of ceramic which is a solid electrolyte, said method comprising the steps of: selecting a primary lead connection wire of a material capable of withstanding the firing and operating temperatures of said sensor and of a thickness sufficient to withstand normal flexing during the life of the sensor, but too great to be capable of being retained in a bonded relationship to said ceramic body by a glass frit seal when differential expansion takes place between the ceramic and primary lead wire during a plurality of heating cycles; forming an opening in the reference end of said ceramic body while said body is in a green or unfired state, said opening being sized so that shrinkage of said body during firing will cause the internal wall of said opening to mechanically clamp said primary lead wire; selecting a secondary lead wire which is capable of resisting the firing and operating temperatures of said sensor and is thin enough so as to be capable of being retained in a bonded relationship to said ceramic body by a glass frit seal during a plurality of heating cycles, said secondary wire being too thin to withstand repeated flexing; placing at least the primary lead wire in said opening; firing said ceramic body to cure said ceramic and shrink the sides of said opening into clamping engagement with said primary wire; attaching one end of said secondary wire to a non-flexing portion of said primary wire; placing the other end of said secondary wire in contact with one end of a glass frit conductive lead stripe on the surface of the tubular body which is joined at its other end to an electrode coating on the solid electrolyte; covering said other end of said secondary wire with a paste layer of glass frit conductive material; and again firing the ceramic body to fuse said paste layer to said secondary wire.

7. The method of claim 6 wherein the said one end of said secondary wire is placed within said opening in parallel relationship with said primary lead wire and is attached into tight clamping contact with said primary lead wire and with the sides of said opening when said ceramic shrinks as it is cured by firing.

8. The method of claim 6 wherein the said one end of said secondary wire is attached by welding to said primary wire.

9. The method of claim 6 wherein the said one end of said secondary wire is attached to said primary wire by being wrapped around it and coated with a layer of conductive glass frit paste which fuses the wires together during said last mentioned firing.

10. The method of claim 6 wherein said oxygen sensor is of the type in which the solid electrolyte is a pre-fired stabilized zirconia disc having conductive paste electrodes applied to each of its opposed faces and an adjoining side edge, said method further including the steps of: applying a short length of conductive paste to opposed internal wall portions of the tubular ceramic body while said body is in its green state; positioning said disc so that the electrodes on opposed side edges will engage and fuse to said short lengths of conductive paste when said body is first fired; and applying said glass frit conductive lead stripe on the inside of said tubular ceramic body after said body is first fired.

* * * * *